United States Patent [19]
Kloek

[11] 4,182,623
[45] Jan. 8, 1980

[54] BICYCLOTHIADIAZINONES
[75] Inventor: James A. Kloek, Overland, Mo.
[73] Assignee: Monsanto Company, St. Louis, Mo.
[21] Appl. No.: 819,635
[22] Filed: Jul. 27, 1977
[51] Int. Cl.$^2$ ............................................... A01N 9/12
[52] U.S. Cl. ........................................ 71/91; 544/10; 544/11; 560/125
[58] Field of Search ............................... 71/91; 544/10

[56] References Cited
U.S. PATENT DOCUMENTS 3,629,250  12/1971  Mutsch ................................. 544/10
3,920,641  11/1975  McKendry ............................ 544/10

*Primary Examiner*—Ethel G. Love
*Attorney, Agent, or Firm*—William I. Andress; Donald W. Peterson

[57] ABSTRACT

The disclosure herein relates to novel fused bicyclothiadiazinones wherein carbocyclic or heterocyclic rings are fused to a thiadiazinone ring. Members of this class of compounds have shown biological activity such as herbicidal activity, plant growth regulator activity and cold or heat stress relief in some plants.

9 Claims, No Drawings

BICYCLOTHIADIAZINONES

BACKGROUND OF THE INVENTION

1. Field of the Invention

The invention herein pertains to the field of novel bicyclothiadiazinones and their herbicidal use.

2. Description of the Prior Art

Thiadiazinone dioxides as a class are known compounds. In more particular, unsubstituted or substituted benzothiadiazione dioxides and pyridothiadiazione dioxides have been disclosed in the prior art. Various utilities recited for these compounds include use as pharmaceuticals, e.g., antiphlogistics, antipyretics, analgetics, psycholeptics and as herbicides. Exemplary nd relevant prior art includes an article by Cohen et al in J. Amer. Chem. Soc., 84, 1994, (1962) and the following U.S. Pat. Nos. 3,041,336, 3,217,001, 3,708,277, 3,940,389, 3,920,641 and 3,989,507.

The prior art relevant to thiadiazinone dioxides appears to be devoid of disclosure relevant to fused bicyclothiadiazinone dioxide compounds having a carbocyclic ring, sulfur-containing heterocyclic ring or cerrain nitrogen-containing heterocyclic rings fused to a thiadiazinone ring. It is an object of this invention to provide such novel compounds, members of which have been found to be biologically active.

SUMMARY OF THE INVENTION

The present invention relates to novel bicyclothiadiazinone dioxide compounds, herbicidal compositions containing such compounds as active ingredient and herbicidal method of use of such compositions.

In more particular, the compounds of this invention are those having the formula

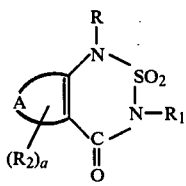

wherein

R, $R_1$ and $(R_2)_a$ independently represent hydrogen, alkyl, alkenyl, alkynyl, alkoxy, alkoxyalkyl, polyalkoxy, cycloalkyl, aryl, aralkyl, alkarylene, acyl, alkoxycarboalkyl or analogs thereof substituted with halo, nitro, hydroxy, cyano, $CF_3$, alkylthio or mono- or dialkylamino or alkanolamino groups;

A comprises an alkylene group having up to 6 carbon atoms or the residue of a heterocyclic ring having up to 7 ring atoms at least one of which is O, $S(O)_x$, $P(O)_y R_3$ or $N(R_3)_z$, where $R_3$ is the same as R–$R_2$;

a is 0–4 x is 0, 1 or 2 and y and z are 0 or 1 provided that when said heterocyclic ring has an $N(R_3)_n$ group in a 6-membered ring, $R_2$ $R_3$ are hydrogen, n is 1, and a is 3.

DESCRIPTION OF PREFERRED EMBODIMENTS

The compounds according to this invention are suitably prepared by cyclizing sulfamoyl esters under base or preferably acid conditions. The precursor sulfamoyl esters to be cyclized are prepared by the regiospecific sulfamoylation of primary enamino esters as will be exemplified below.

EXAMPLE 1

This example illustrates the preparation of 2-(isopropylsulfamido)-1-cyclohexene-1-carboxylic acid ethyl ester, the precursor sulfamoyl ester of the compound of this invention described in Example 2.

To two equivalents of sodium metal dissolved in a convenient amount of ethanol was added one equivalent of 2-(ethoxycarbonylamino)-1-cyclohexene-1-carboxylic acid ethyl ester and the resulting mixture refluxed for 18 hours. After cooling, the solution was poured into twice its volume of water and extracted three times with ether. The extracts were combined, washed with brine, dried over magnesium sulfate and concentrated on a rotary evaporator. The product was recrystallized from an equeous ethanol solution, recovered in 80% yield and identified as ethyl-2amino-1-cyclohexene-1-carboxylate having a melting point of 71–73° C.

N-isopropyl sulfamoyl chloride (7.18 g; 0.05 mol) was added to a solution of 16.90 g (10.10 mol) of ethyl-2-amino-1-cyclohexene-1-carboxyplate. The resulting slurry was stirred at room temperature for 72 hours, then washed with water; the organic layer was dried, filtered and concentrated. The residue was treated with 20% ethyl acetate/80% cyclohexane on dry column silica gel. The product of interest, 2-(isopropyl sulfamido)-1-cyclohexene-1-carboxylic acid ethyl ester, was recovered in 85% yield.

| Anal.: Calc'd for $C_{12}H_{22}N_2O_4S_1$ | Calc'd | Found |
|---|---|---|
| C | 49.63 | 49.36 |
| H | 7.64 | 7.76 |
| N | 9.65 | 9.50 |

EXAMPLE 2

This example describes the preparation of 3-isopropyl-5,6,7,8-tetrahydro-2,1,3-benzothiadiazin-4(3H)one-2,2-dioxide, a compound according to this invention, by the preferred acid-catalyzed ring closure of the precursor sulfamoyl esters prepared in accordance with the process described in Example 1.

A solution of 0.75 g of 2-(isopropyl sulfamido)-1-cyclohexene-1-carboxylic acid, t-butyl ester in 5 mil of trifluoroacetic acid and 5 mil of trifluoroacetic anhydride (TFA/TFAA) was stirred at room temperature for 5 minutes. The solvents were evaporated and the resulting solid triturated with hexane to provide 0.5 g (87%) of the cyclic sulfamide named in the preceding paragraph; mp 188–192°.

| Anal. Calc'd for $C_{10}H_{16}N_2O_3S_1$ | Calc'd | Found |
|---|---|---|
| C | 49.16 | 49.19 |
| H | 6.60 | 6.60 |
| N | 11.47 | 11.42 |

Alternative in less-preferred embodiments cyclizations of the precursor sulfamoyl esters such as that prepared in Example 1 are accomplished under basic conditions. Thus, reacting such esters with methanolic sodium hydroxide or ethanolic potassium hydroxide will also effect ring closure. In some instances, where the substituent on the terminal nitrogen (N-3) of the sulfamido group is a non-bulky substituent, e.g., a primary alkyl group such as a methyl or ethyl radical, ring closure is smoothly effected by a 5% sodium hydroxide solution. In other instances where the N-3 substituent is a branched chain or bulky group, e.g., a longer primary alkyl, e.g., n-butyl or a secondary alkyl radical such as isopropyl or a tertiary alkyl groups such as tert-butyl, more severe conditions are required such as refluxing in ethanolic potassium hydroxide or treating with phosgene. In some cases, ring closure is direct; in other cases, the ester is saponified to the corresponding isolable acid which may then be treated under acid conditions, e.g., with TFA/TFAA, to effect ring closure.

In further specific embodiments exemplary compounds according to this invention listed in Examples 3-31 in the table are prepared according to the general procedures described in Examples 1 and 2, but substituting the appropriate starting materials corresponding to the final product, solvents, reaction conditions of times, pressures, temperatures, etc., as will be appreciated by those skilled in the art. Thus, depending upon the physical characteristics and properties of the starting materials and products the precursor sulfamoyl esters may be prepared by reacting the starting materials, viz., the 2-aminocyclohexenecarboxylate and sulfamoyl chlorides at temperatures generally within the range of about $-78°$ C. to $150°$ C., and preferably from about $0°$ C. to $35°$ C., at subatmospheric, atmospheric or superatmospheric pressures and reaction times of from about 1 to 72 hours. The thus-prepared sulfamoyl esters are then subjected to ring closures at temperatures within the general range of about $-78°$ C. to $150°$ C. and preferably from about $0°$ C. to $100°$ C. at subatmospheric, atmospheric or superatmospheric pressures and times within the range of from about 0.1 to 72 hours; although some of these cyclizations occur instantaneously.

The final product may be recovered by conventional techniques such as distillation, recrystallization, etc. Suitable solvents herein include alcohols, alkanes, halogenated alkanes, cycloalkanes, esters of lower aliphatic alcohols and acids, aromatic hydrocarbons or mixtures thereof. Exemplary solvents include aqueous, ethanol, pentane, cyclohexane, methylcyclohexane, chloroform, ethyl acetate, toluene, the xylenes, ether/pentane, ethanol/nitromethane, etc.

TABLE 1

| Example No | Compound | Empirical Formula | M.P. °C. | Element | Analysis Calculated | Found | Yield % |
|---|---|---|---|---|---|---|---|
| 3 | 5,6,7,8-tetrahydro-3-Ethyl-benzo(1H)-2,1,3-thiadiazin-4-one-2,2-dioxide | $C_9H_{14}N_2O_3S_1$ | 208-210 | C<br>H<br>N | 46.78<br>6.17<br>12.21 | 46.94<br>6.13<br>12.16 | 71 |
| 4 | 3-methyl-5,6,7,8-tetrahydro-benzo(1H)-2,1,3-thiadiazin-4-one-2,2-dioxide | $C_8H_{12}N_2O_3S_1$ | 215-219 | C<br>H<br>N | 44.43<br>5.59<br>12.95 | 44.28<br>5.65<br>12.93 | 88 |
| 5 | 1H-2,1,3-benzothiadiazin-4(3H)-one,5,6,7,8-tetrahydro,3-Ethyl-6-methyl,2,2-dioxide | $C_{10}H_{16}N_2O_3S$ | 209-210 | C<br>H<br>N | 49.16<br>6.60<br>11.47 | 48.90<br>6.64<br>11.48 | 62 |
| 6 | 1H-2,1,3-cyclopenta-thiadiazin-4(3H)-one,3-Ethyl-1,5,6,7-tetrahydro,2,2-dioxide | $C_8H_{12}N_2O_3S$ | 175-76 | C<br>H<br>N | 44.43<br>5.59<br>12.95 | 44.42<br>5.61<br>12.93 | |
| 7 | 1H-2,1,3-benzothiadiazin-4(3H)-one,6-isopropyl,3-methyl,5,6,7,8-tetrahydro,2,2-dioxide | $C_{11}H_{18}N_2O_3S$ | 191-193 | C<br>H<br>N | 51.14<br>7.02<br>10.84 | 50.99<br>7.09<br>10.76 | 27 |
| 8 | 1H-2,1,3-benzothiadiazin-4(3H)-one,6-isopropyl,3-ethyl,5,6,7,8-tetrahydro,2,2-dioxide | $C_{12}H_{20}N_2O_3S$ | 192-194 | C<br>H<br>N | 52.92<br>7.40<br>10.29 | 52.96<br>7.43<br>10.25 | 37 |
| 9 | 1H-2,1,3-benzothiadiazin-4(3H)-one,3,7-dimethyl,5,6,7,8-tetrahydro,2,2-dioxide | $C_9H_{14}N_2O_3S$ | 207-208 | C<br>H<br>N | 41.94<br>6.10<br>12.16 | 41.68<br>6.13<br>12.06 | 92 |
| 10 | 1H-2,1,3-benzothiadiazin-4(3H)one,3-ethyl,7-methyl,5,6,7,8-tetrahydro,2,2-dioxide | $C_{12}H_{20}N_2O_3S$ | | C<br>H<br>N | 49.16<br>6.60<br>11.47 | 48.98<br>6.63<br>11.40 | 27 |
| 11 | 1H-2,1,3-benzothiadiazin-4(3H)-one,3-n-butyl,7-methyl,5,6,7,8-tetrahydro,2,2-dioxide | $C_{12}H_{20}N_2O_3S$ | 128-130 | C<br>H<br>N | 52.92<br>7.40<br>10.29 | 52.93<br>7.43<br>10.27 | 52 |
| 12 | 1H-2,1,3-benzothiadiazin-4(3H)-one,3-n-butyl,5,6,7,8-tetrahydro,2,2-dioxide | $C_{11}H_{18}N_2O_3S$ | 153-155 | C<br>H<br>N | 51.14<br>7.02<br>10.84 | 51.01<br>7.06<br>10.91 | 53 |
| 13 | 1H-2,1,3-benzothiadiazin-4(3H)-one,3-methyl,7-t-butyl,5,6,7,8-tetrahydro,2,2-dioxide | $C_{12}H_{20}N_2O_3S$ | 231-233 | C<br>H<br>N | 52.92<br>7.40<br>10.29 | 52.95<br>7.43<br>10.24 | 83 |
| 14 | 1H-2,1,3-benzothiazin-4(3H)-one,3-ethyl,7-t-butyl,5,6,7,8-tetrahydro,2,2-dioxide | $C_{12}H_{22}N_2O_3S$ | 216-218 | C<br>H<br>N | 54.82<br>7.74<br>9.78 | 54.37<br>7.74<br>9.80 | 41 |
| 15 | 1H-2,1,3-benzothiadiazin-4(3H)-one,3-isopropyl,6-t-butyl,5,6,7,8-tetrahydro,2,2-dioxide | $C_{14}H_{24}N_2O_3S$ | 214 | C<br>H<br>N | 55.97<br>8.05<br>9.32 | 55.97<br>8.07<br>9.36 | 43 |
| 16 | 1H-2,1,3-benzothiadiazin-4(3H)-one,3-cyclohexyl,5,6,7,8-tetrahydro,2,2-dioxide | $C_{13}H_{20}N_2O_3S$ | 208-209 | C<br>H<br>N | 54.91<br>7.09<br>9.85 | 54.78<br>7.17<br>9.76 | 79 |
| 17 | 1H,5H-thiopyrano[3,4-e]2,1,3-thiadiazin-4(3H)-one,3-methyl,7,8-dihydro,2,2-dioxide | $C_7H_{10}N_2O_3S_2$ | 205-207 | C<br>H<br>N | 35.88<br>4.30<br>11.96 | 35.89<br>4.32<br>12.03 | 37 |
| 18 | 1H,5H-thiopyrano[3,4-e]2,1,3- | $C_8H_{12}N_2O_3S_2$ | 196-198 | C | 38.65 | 38.81 | 35 |

TABLE 1-continued

| Example No | Compound | Empirical Formula | M.P. °C. | Element | Calculated | Found | Yield % |
|---|---|---|---|---|---|---|---|
|  | thiadiazin-4(3H)-one,3-ethyl, 7,8-dihydro,2,2-dioxide |  |  | H | 4.87 | 4.90 |  |
|  |  |  |  | N | 11.28 | 11.32 |  |
| 19 | 1H-pyrido[3,4-e]2,1,3-thiadiazin-4(3H)-one,3-methyl,6-acetyl,5,6,7,8-tetrahydro,2,2-dioxide | $C_9H_{13}N_3O_4S$ | 199-201 | C | 41.69 | 41.69 | 61 |
|  |  |  |  | H | 5.05 | 5.08 |  |
|  |  |  |  | N | 16.21 | 16.23 |  |
| 20 | 1H-pyrido[3,4-e]2,1,3-thiadiazin-4(3H)-one,3-n-butyl,6-acetyl,5,6,7,8-tetrahydro, 2,2-dioxide | $C_{12}H_{19}N_3O_4S$ | glass | C | 47.83 | 48.65 | 40 |
|  |  |  |  | H | 6.36 | 6.57 |  |
|  |  |  |  | N | 13.94 | 13.08 |  |
| 21 | 1H,5H-thiopyrano[3,4-e]2,1,3-thiadiazin-4(3H)-one,3-n-butyl,7,8-dihydro,2,2-dioxide | $C_{10}H_{10}N_2O_3S_2$ | 154-157 | C | 43.46 | 43.57 | 38 |
|  |  |  |  | H | 5.84 | 5.87 |  |
|  |  |  |  | N | 10.14 | 10.19 |  |
| 22 | 1H,5H-thiopyrano[3,4-e]2,1,3-thiadiazin-4(3H)-one,3-isopropyl,7,8-dihydro,2,2-dioxide | $C_9H_{14}N_2O_3S_2$ | 190 | C | 41.20 | 41.09 |  |
|  |  |  |  | H | 5.38 | 5.38 |  |
|  |  |  |  | N | 10.68 | 10.75 |  |
| 23 | 1H-pyrido[3,4-e]2,1,3-thiadiazin-4(3H)-one,3-ethyl,6-acetyl,5,6,7,8-tetrahydro,2,2-dioxide | $C_{10}H_{15}N_3O_4S$ | 184-186 | C | 43.95 | 43.77 | 38 |
|  |  |  |  | H | 5.53 | 5.53 |  |
|  |  |  |  | N | 15.37 | 15.33 |  |
| 24 | 1H-thieno[3,2-d]-1,2,6-thiadiazin-4(3H)-one,3-n-butyl, 2,2-dioxide | $C_9H_{12}N_2O_3S_2$ | 153-155 | C | 41.52 | 41.48 | 72 |
|  |  |  |  | H | 4.65 | 4.69 |  |
|  |  |  |  | N | 10.76 | 10.76 |  |
| 25 | 1H-thieno[3,2-d]-1,2,6-thiadiazin-4(3H)-one,3-ethyl, 2,2-dioxide | $C_7H_8N_2O_3S_2$ | 196-198 | C | 36.20 | 36.22 | 62 |
|  |  |  |  | H | 3.47 | 3.49 |  |
|  |  |  |  | N | 12.06 | 12.01 |  |
| 26 | 1H-thieno[3,2-d]-1,2,6-thiadiazin-4(3H)-one,3-isopropyl, 2,2-dioxide | $C_8H_{10}N_2O_3S_2$ | 138-140 | C | 38.01 | 38.82 | 57 |
|  |  |  |  | H | 4.09 | 4.15 |  |
|  |  |  |  | N | 11.37 | 11.38 |  |
| 27 | 1H,9H-(1,2,6-thiadiazin-(3,4-d)indol-4(3H)one,3-butyl,2,2-dioxide | $C_{13}H_{15}N_3O_3S$ | 179-181 | C | 53.18 | 52.94 | 26 |
|  |  |  |  | H | 5.11 | 5.19 |  |
|  |  |  |  | N | 14.22 | 14.28 |  |
| 28 | 1H,7H-pyrazole[5,4-c](1,2,6)-thiadiazin-4(3H)-one,3-methyl, 2,2-dioxide hydrate | $C_5H_8N_1O_4S$ | 245 | C | 27.37 | 27.20 | 31 |
|  |  |  |  | H | 3.64 | 3.72 |  |
|  |  |  |  | N | 25.45 | 25.41 |  |
| 29 | 1H,7H-pyrazole[5,4-c](1,2,6)-thiadiazin-4(3H)-one,3-ethyl, 2,2-dioxide | $C_6H_8N_4O_3S_1$ | 164-167 | C | 33.33 | 33.47 | 45 |
|  |  |  |  | H | 3.73 | 4.03 |  |
|  |  |  |  | N | 25.91 | 25.19 |  |
| 30 | 1H,7H-pyrazole[5,4-c](1,2,6)-thiadiazin-4(3H)-one,3-n-butyl, 2,2-dioxide | $C_8H_{12}N_4O_3S_1$ | 182-185 | C | 39.34 | 39.39 | 74 |
|  |  |  |  | H | 4.92 | 4.93 |  |
|  |  |  |  | N | 22.95 | 22.92 |  |
| 31 | 1H,7H-pyrazole[5,4-c](1,2,6)-thiadiazin-4(3H)-one,3-isopropyl,2,2-dioxide | $C_7H_{10}N_4O_3S_1$ |  | C | — | — | — |
|  |  |  |  | H | — | — |  |
|  |  |  |  | N | — | — |  |

In the compounds of this invention according to the above structural formula the $R_1$ substituent derives from the particular sulfamoyl halide starting material used to prepare the precursor sulfamoyl ester. In general, the $R_2$ substituents derive from the particular enamino ester starting material. However, additional or different $R_2$ members (particularly on the hetero atom) and R members also, may be substituted on the fully cyclized molecule; the following examples illustrate various embodiments thereof.

EXAMPLE 32

One equivalent of the compound of Example 11 (refer to the above table) was slurried with one equivalent of isopropyl amine in sufficient ether/ethyl acetate solvent to dissolve the amine. The product was stirred overnight, then separated from the solvent and identified by NMR analysis as the isopropylamine salt of 5,6,7,8-tetrahydro(1H)-benzo-2,1,3-thiadiazin-4-one, 3-n-butyl, 2,2-dioxide; empirical formula $C_{14}H_{29}N_3O_3S$.

EXAMPLE 33

The procedure described in Example 32 was repeated substituting ethanol amine in place of isopropyl amine. The product of this example, identified by NMR, was the ethanol amine salt of 5,6,7,8-tetrahydro(1H)-benzo-2,1,3-thiadiazin-4-one, 3-n-butyl,2,2-dioxide; empirical formula $C_{13}H_{25}N_3O_4S$.

EXAMPLE 34

Repeating the procedure of Examples 33 and 34, but substituting the compound of Example 3 and triethyl amine as starting materials, the triethyl amine salt of 5,6,7,8-tetrahydro 1(H)-benzo-2,1,3-thiadiazin-4-one,3-ethyl,2,2-dioxide, a product of empirical formula $C_{15}H_{29}N_2O_3S$, was produced.

EXAMPLE 35

This example illustrates the acylation of previously cyclized products according to this invention.

To one equivalent of the product of Example 3 was added one equivalent of triethylamine and one equivalent of monochloroacetyl chloride dissolved in methylene chloride. The resulting slurry was stirred overnight at room temperature. Water was then added, the layers separated and the organic layer extracted with 5% NaOH, dried, filtered and concentrated. The residue was recrystallized in methylcyclohexane.

The product obtained in 82% yield was identified by NMR and elemental analysis as 1-(α-chloroacetyl)-3-ethyl-5,6,7,8-tetrahydrobenzo-2,1,3-thiadiazin-4-one,2,2-dioxide; m.p. 76°-78°.

| Anal.: Calc'd for $C_{11}H_{15}ClN_2O_4S$ | Calc'd | Found |
|---|---|---|
| C | 43.07 | 42.93 |
| H | 4.93 | 4.96 |
| N | 9.03 | 9.10 |

EXAMPLE 36

Following the general procedure described in Example 35, but substituting the compound of Example 11 as starting material, the produce 1-(α-chloroacetyl)-3-n-butyl-5,6,7,8-tetrahydrobenzo-2,1,3-thiadiazin-4-one,2,2-dioxide was prepared and recovered in 30% yield, m.p. 69°–71°.

| Anal.: Calc'd for $C_{13}H_{19}ClN_2O_4S$ | Calc'd | Found |
|---|---|---|
| C | 46.78 | 46.70 |
| H | 5.70 | 5.75 |
| N | 8.40 | 8.39 |

EXAMPLE 37

The cyclized thiadiazinone compounds of this invention may be alkylated to obtain corresponding substituted N-1 derivatives.

One equivalent each of the compound of Example 3, triethylamine and monochloroethyl acetate were slurried in methylene chloride, stirred overnight, then mixed with water; the layers were separated, the organic layer extracted with 5% NaOH, dried, filtered and concentrated.

The product obtained in 22% yield was identified by NMR and elemental analysis as 1H-2,1,3-benzothiadiazin-4(3H)-one,1-(acetic acid ethyl ester)-3-ethyl,5,6,7,8-tetrahydro,2,2-dioxide.

| Anal.: Calc'd for $C_{13}H_{20}N_2O_5S$ | Calc'd | Found |
|---|---|---|
| C | 49.35 | 49.11 |
| H | 6.37 | 6.47 |
| N | 8.96 | 8.76 |

EXAMPLE 38

Following the general procedure of Example 37, one equivalent of the compound of Example 3 and one equivalent each of triethylamine and chloromethyl/methyl/ether were reacted. The product was recrystallized from a methylcyclohexane/ether solvent and recovered in 88% yield.

The product, analyzed by NMR and elemental analysis, was identified as 1-methoxymethyl-3-ethyl-5,6,7,8-tetrahydrobenzo-2,1,3-thiadizin-4-one-2,2-dioxide.

| Anal.: Calc'd for $C_{11}H_{18}N_2O_4S$ | Calc'd | Found |
|---|---|---|
| C | 47.16 | 47.93 |
| H | 6.61 | 6.66 |
| N | 10.21 | 10.21 |

EXAMPLE 39

One equivalent of the compound of Example 3 was slurried in ethyl acetate with 2 equivalents of butyl vinyl ether and a catalytic amount of $PCl_5$. After refluxing for 2 hours, the solution was cooled, washed with water, extracted with 5% NaOH, dried, filtered and stripped. The residue was taken up in boiling pentane, decanted from the insoluble fraction and concentrated into an oily product of 36% yield.

| Anal.: Calc'd for $C_{15}H_{26}N_2O_4S$ | Calc'd | Found |
|---|---|---|
| C | 54.52 | 54.78 |
| H | 7.93 | 7.96 |
| N | 8.48 | 8.38 |

EXAMPLE 40

One equivalent of the compound of Example 11 and one equivalent of 85% KOH in dimethylformamide was heated to 60° C. and held there until no more solid KOH was visible. Then one equivalent of 1,1,2,3-tetrachloro-1-propene was added and the temperature held at 60° C. overnight. The resulting slurry was filtered and the filtrate poured into ice water and extracted 3 times with ether. The ether extracts were dried, filtered and stripped with the residual oil as product.

Upon analysis, the product in 31% yield was identified as 1H-2,1,3-benzothiadiazin-4(3H)-one-3-n-butyl-2,2-dioxide,5,6,7,8-tetrahydro-1-(2,3,3-trichloroallyl).

| Anal.: Calc'd for $C_{14}H_{19}Cl_3N_3O_3S$ | Calc'd | Found |
|---|---|---|
| C | 41.84 | 42.21 |
| H | 4.73 | 4.53 |
| N | 6.97 | 6.80 |

EXAMPLE 41

To an ice cold solution of 5.55 g of the compound of Example 21 in 400 ml of methylene chloride was added a solution of 3.66 g m-chloroperbenzoic acid in 60 ml of methylene chloride. After stirring at 0° C. for 18 hours, the solution was extracted 3 times with saturated sodium bicarbonate. These extracts were combined, acidified with concentrated hydrochloric acid, and the resulting solid filtered. The solid was dried and recrystallized from ethylenedichloride to afford 1H,5H-thiopyrano-[3,4-d]-2,1,3-thiadiazin-4(3H)-one,3-n-butyl-7,8-dihydro,2,2,6-trioxide, in 51% yield; m.p. 162°–164°.

| Anal.: Calc'd for $C_{10}H_{16}N_2O_4S_2$ | Calc'd | Found |
|---|---|---|
| C | 41.08 | 41.11 |
| H | 5.52 | 5.53 |
| N | 9.58 | 9.50 |

EXAMPLE 42

To a stirred suspension of 2.76 g of the compound of Example 21 in 10 ml of glacial acetic acid was added 5 ml of 40% peracetic acid. After 10 minutes, a solid had precipitated. The product was filtered, and recrystallized from acetonitrile to provide 890 mg of 1H,5H-thiopyrano[3,4-d]-2,1,3-thiadiazin-4(3H)-one,3-n-butyl-7,8,dihydro,2,2,6,6-tetraoxide, in 28% yield; m.p. 192–195°.

| Anal.: Calc'd for $C_{10}H_{16}N_2O_5S_2$ | Calc'd | Found |
|---|---|---|
| C | 32.95 | 32.89 |
| H | 5.23 | 5.23 |

-continued

| Anal.: Calc'd for $C_{10}H_{16}N_2O_5S_2$ | Calc'd | Found |
|---|---|---|
| N | 9.08 | 9.05 |

EXAMPLE 43

The compound of Example 20 was dissolved in 10 ml of 95% ethanol and the temperature was raised to reflux. 10 ml of concentrated HCl was added and reflux continued for 4–5 hours. The solution was allowed to stand at room temperature for 10 days, then the crystallized product was filtered from the reaction mixture.

Upon analysis the product in 31% yield, was identified as 1(H)pyrido(3,4-d)-2,1,3-thiadiazin-4(3H)-one-3-n-butyl,2,2-dioxide-5,6,7,8-tetrahydro HCl salt; m.p. 184°–187°.

| Anal.: Calc'd for $C_{10}H_{18}ClN_3O_3S$ | Calc'd | Found |
|---|---|---|
| C | 40.61 | 39.56 |
| H | 6.13 | 6.35 |
| N | 14.21 | 13.80 |

EXAMPLE 44

The post-emergence herbicidal activity of various compounds of this invention is demonstrated as follows. The active ingredients are applied in spray form to 14–21 day-old speciments of various plant species. The spray, a water or organic solvent-water solution containing active ingredient and a surfactant (35 parts butylamine salt of dodecylbenzenesulfonic acid and 65 parts tall oil condensed with ethylene oxide in the ratio of 11 moles ethylene oxide to 1 mole tall oil), is applied to the plants in different sets of pans at several rates (kg per hectare) of active ingredient. The treated plants are placed in a greenhouse and the effects are observed and recorded after approximately 2 weeks or approximately 4 weeks. The data is given in Table 2. A dash (-) denotes that the species was not in the test or was not tested at a given rate. The test compounds are designated by example numbers.

The post-emergence herbicidal activity index used in Table 2 is as follows:

| Plant Response | Index |
|---|---|
| 0–24% Injury | 0 |
| 25–49% Injury | 1 |
| 50–74% Injury | 2 |
| 75–99% Injury | 3 |
| All Killed | 4 |

TABLE 2

Post-emergence Herbicidal Activity

| Compound of Example | Rate Kg/Ha | Soybean | Sugarbeet | Wheat | Rice | Sorghum | Cocklebur | Wild Buckwheat | Morninglory | Hemp Sesbania | Lambsquarters | Smartweed | Velvetleaf | Downy Brome | Panicum Spp. | Barnyardgrass | Crabgrass | Canada Thistle | Nutsedge | Quackgrass | Johnsongrass |
|---|---|---|---|---|---|---|---|---|---|---|---|---|---|---|---|---|---|---|---|---|---|
| 2 | 11.2 | — | — | — | — | — | 2 | — | 0 | — | 2 | 2 | 2 | 0 | — | — | — | — | 0 | 0 | — |
|  | 5.60 | — | — | — | — | — | 2 | — | 0 | — | 2 | 2 | — | 0 | — | — | — | 0 | 0 | 0 | — |
| 9 | 11.2 | — | — | — | — | — | 1 | — | 0 | — | — | 0 | 0 | 0 | — | 0 | — | 0 | 0 | 0 | 0 |
| 12 | 11.2 | — | 0 | 0 | 0 | — | — | — | 0 | 0 | 3 | 3 | 0 | 0 | — | — | — | — | 0 | 0 | 0 |
|  | 5.60 | 1 | 0 | 0 | 0 | 1 | 1 | 1 | 0 | 0 | 2 | 4 | 0 | 1 | 1 | 0 | 1 | 1 | 0 | 0 | 0 |
| 16 | 11.2 | — | — | — | — | — | 0 | — | 0 | — | 1 | 2 | 0 | 0 | — | 0 | — | 0 | 0 | 0 | 0 |
| 17 | 11.2 | — | — | — | — | — | 1 | — | 0 | — | — | 1 | 1 | 0 | — | — | — | 0 | 0 | — | 0 |
| 18 | 11.2 | — | — | — | — | — | 2 | — | 0 | — | 4 | 4 | 1 | 0 | — | — | — | — | 0 | 0 | 0 |
| 32 | 11.2 | 1 | — | — | — | — | 2 | 0 | 1 | — | 4 | 4 | 3 | 0 | — | 3 | — | — | 0 | 0 | 0 |
|  | 5.60 | — | — | — | — | — | 0 | — | 0 | — | 2 | 2 | 0 | 0 | — | — | — | — | 0 | 0 | 0 |
| 33 | 11.2 | — | 2 | — | — | — | 2 | 0 | 0 | 2 | 1 | 1 | 0 | 0 | 0 | 0 | — | — | 0 | 0 | 0 |
| 34 | 11.2 | — | 1 | — | — | — | — | 0 | 1 | 1 | 2 | 0 | 1 | 0 | 0 | 0 | — | 1 | 0 | — | 0 |
| 35 | 5.60 | 0 | — | — | — | — | 0 | — | 0 | — | 0 | 4 | 0 | 0 | — | 0 | 0 | 4 | 0 | 0 | 0 |
| 36 | 1.12 | — | — | — | — | — | 2 | — | 1 | — | 3 | 0 | 2 | 1 | — | — | — | — | 0 | 0 | 0 |
| 38 | 11.2 | — | — | — | — | — | — | — | — | — | — | 0 | 0 | — | — | — | — | 1 | 0 | 0 | — |
| 4 | 11.2 | 0 | 0 | 0 | — | 0 | 0 | 0 | 0 | 0 | — | 0 | 0 | 0 | 0 | 0 | — | 0 | 0 | 0 | — |
| 11 | 5.60 | — | 0 | 0 | — | 0 | 0 | 0 | 0 | 1 | 0 | 0 | 0 | 0 | 0 | 0 | — | — | — | — | — |

In addition to having post-emergent herbicidal activity as shown in Table 2, some of the compounds of this invention have shown efficacy as heat or stress reducers in plants. For example, the compound of Example 24 has reproducibly relieved cold stress on soybean seedlings. The compound of Example 23 has reproducibly reduced heat stress in duckweed (used as screening plant).

In addition, some compounds of this invention have shown plant growth regulator activity. For example, the compound of Example 16 produced morphological changes, e.g., leaf alteration and leaf distortion on soybean plants.

The active ingredient herein can be admixed with one or more adjuvants which can be solid or liquid extenders, carriers, diluents, conditioning agents and the like to form herbicidal compositions. Herbicidal compositions containing the active ingredients of this invention can be formulated with or in the form of granules, wettable powders, aqueous suspensions, dust formulations, emulsifiable oils and solutions in solvents. In general, these formulations can all contain one or more surface-active agents.

Surface-active agents which can be used in herbicidal formulations are well known to those skilled in the art and have been well documented in patents, bulletins and textbooks.

The preparation, formulation and particle size of the granules, wettable powders, aqueous suspensions, dusts, emulsifiable oils and solutions in solvents are also well known to those skilled in the art and well documented.

The active ingredient is usually present in the herbicidal compositions in a range of about 0.5 to 95 parts by weight per 100 parts by weight of wettable powder and dust formulations and from about 5 to 95 parts by weight per 100 parts by weight emulsifiable oil formulations. Formulations containing more or less than the above quantities of active ingredient can easily be prepared by those skilled in the art.

The quantity of active ingredient to be used in the field may vary within certain limits depending upon variables known to those in the art, e.g., condition of the soil, climate, plants, etc. In general, however, amounts ranging from about 0.1 to 44.8 or more kg/ha should be adequate; a preferred range being from about 1.0 to 15.0 kg/ha or suitably, an amount within the range of from 2.0 to 12.0 kg/ha.

Modes of application of the herbicidal compositions of this invention to the plant are well known to those skilled in the art. The application of liquid and particulate solid herbicidal formulations to the above-ground portions of plants can be carried out by conventional methods, e.g., power dusters, boom and hand sprayers and spray dusters.

The phytotoxic compositions of this invention can also contain other additaments, for example, fertilizers, safening agents, other phytotoxicants, pesticides and the like, used as adjuvant or in combination with any of the above-described adjuvants.

The compounds of this invention may be used in combination with known herbicides in order to provide enhanced biological effectiveness. The use of various herbicides in combination at the time of a single application or sequentially is common in practice. Herbicides which may be used in combination with the compounds of this invention include but are not limited to:

Substituted phenoxyaliphatic acids such as 2,4-dichlorophenoxyacetic acid; 2,4,5-trichlorophenoxyacetic acid, 2-methyl-4-chlorophenoxyacetic acid and the salts, esters and amides thereof; symmetrical or asymmetrical triazine derivatives, such as 2-chloro-4-ethylamino-6-isopropylamino-s-triazine; 2,4-bis(isopropylamino)-6-methoxy-s-triazine and 2-methylmercapto-4,6-bis(isopropylamino)-s-triazine; urea derivatives such as 3-(3,4-dichlorophenyl)-1,1-dimethylurea and 3-(m-trifluoromethylphenyl)-1,1-dimethylurea and 3-(3,4-dichlorophenyl)-1-methoxy-1-methylurea;
pyridylium derivatives such as 1:1'-ethylene-2,2-dipyridylium dihalide; acetanilides such as N-isopropyl-α-chloroacetanilide, and 2-chloro-2',6'-diethyl-N-methoxymethyl acetanilide; acetamides such as N,N-diallyl-α-chloroacetamide, carbamates such as ethyl-N,N-di-n-propylthiolcarbamate, and 2,3-dichloroallyl diisopropylthiolcarbamate; substituted uracils such as 5-bromo-3-sec-butyl-6-methyluracil, substituted anilines such as N,N-dipropyl-α,α,α-trifluoro-2,6-dinitro-p-toluidine; pryidazone derivatives such as 5-amino-4-chloro-2-phenyl-3-(2H)-pyridazinone; diphenyl ethers which may be unsubstituted or substituted with halogen, nitro, hydroxy, alkylthio, trifluoromethyl, cyano, alkyl, alkoxy, etc. groups; N-(phosphonomethyl)glycine and its $C_{1-6}$ monoalkyl amine and alkali metal salts and combinations thereof in ratios of 1–4 to 4–1 of other herbicidal compounds, which may be selected from those exemplified above.

Fertilizers useful in combination with the active ingredients include, for example ammonium nitrate, urea and superphosphate. Other useful additaments include materials in which plant organisms take root and grow such as compost, manure, humus, sand and the like.

While the illustrative embodiments of the invention have been described hereinbefore with particularlity, it will be understood that various other modifications will be apparent to and can readily be made by those skilled in the art without departing from the scope and spirit of the invention. Accordingly, it is not intended that the scope of the claims appended hereto be limited to the examples and description set forth herein but rather the claims be construed as encompassing all the features of patentable novelty which reside in the present invention including all features which would be treated as equivalents thereof by those skilled in the art to which the invention pertains.

I claim:

1. A compound of the formula

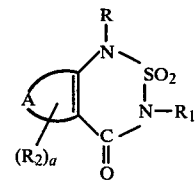

wherein
R, $R_1$ and $R_2)_a$ independently represent hydrogen, lower alkyl, alkenyl, alkynyl, alkoxy, alkoxyalkyl, polyalkoxy, cycloalkyl, aromatic hydrocarbon, lower alkanoyl, alkoxycarboalkyl or said R terms substituted with halo, nitro, hydroxy, cyano, $CF_3$, lower alkylthio or lower mono- or dialkylamino or alkanolamino groups;

A consisting essentially of a heterocyclic residue having up to 7 ring atoms containing only $S(O)_x$ as the hetero moiety;

a is 0-4 and x is 0, 1 or 2.

2. Compounds according to claim 1 wherein R is hydrogen and $R_1$ is alkyl.

3. Compound according to claim 2 which is 1H-thieno-[3,2-d]-1,2,6-thiadiazin-4(3H)-one,3-n-butyl,2,2-dioxide.

4. Compositions comprising a herbicidally effective amount of a compound of the formula

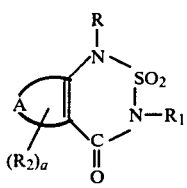

wherein

R, $R_1$ and $(R_2)_a$ independently represent hydrogen, lower alkyl, alkenyl, alkynyl, alkoxy, alkoxyalkyl, polyalkoxy, cycloalkyl, aromatic hydrocarbon, lower alkanoyl, alkoxycarboalkyl or said R terms substituted with halo, nitro, hydroxy, cyano, $CF_3$, lower alkylthio or lower mono- or dialkylamino or alkanolamino groups;

A consisting essentially of a heterocyclic residue having up to 7 ring atoms containing only $S(O)_x$ as the hetero moiety;

a is 0-4;

x is 0, 1 or 2 and an inert adjuvant therefor.

5. Composition according to claim 4 wherein in said compound R is hydrogen and $R_1$ alkyl.

6. Composition according to claim 5 in which said compound is 1H-thieno-[3,2-d]-1,2,6-thiadiazin-4(3H)-one, 3-n-butyl, 2,2-dioxide.

7. Method for selectively controlling undesired plants in the presence of crop plants which comprises applying to the locus thereof a herbicidally-effective amount of a compound of the formula

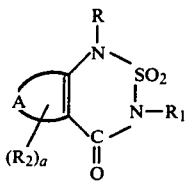

wherein

R, $R_1$ and $(R_2)_a$ independently represent hydrogen, lower alkyl, alkenyl, alkynyl, alkoxy, alkoxyalkyl, polyalkoxy, cycloalkyl, aromatic hydrocarbon, lower alkanoyl, alkoxycarboalkyl or said R terms substituted with halo, nitro, hydroxy, cyano, $CF_3$, lower alkylthio or lower mono- or dialkylamino groups;

A consisting essentially of a heterocyclic residue having up to 7 ring atoms containing only $S(O)_x$ as the hetero moiety;

a is 0-4;

x is 0, 1 or 2 and an inert adjuvant therefor.

8. Method according to claim 7 wherein in said compound, R is hydrogen and $R_1$ is alkyl.

9. Method according to claim 8 in which said compound is 1H-thieno-[3,2-d]-1,2,6-thiadiazin-4(3H)-one,3-n-butyl,2,2-dioxide.

* * * * *

UNITED STATES PATENT AND TRADEMARK OFFICE
CERTIFICATE OF CORRECTION

PATENT NO. : 4,182,623

DATED : January 8, 1980

INVENTOR(S) : James Kloek

It is certified that error appears in the above–identified patent and that said Letters Patent are hereby corrected as shown below:

Column 1, line 18 "84" should read -- $\underline{84}$ --.

Column 2, line 23 "(10.10 mol)" should read -- (0.10 mol) --.

Column 14, line 59 "$R_2)_a$" should read -- $(R_2)_a$ --.

Column 14, line 62 "terms" should read -- groups --.

Column 15, line 36 "$R_1$ alkyl" should read -- $R_1$ is alkyl --.

Signed and Sealed this

*Twenty-fourth* Day of *June 1980*

[SEAL]

Attest:

SIDNEY A. DIAMOND

*Attesting Officer*    *Commissioner of Patents and Trademarks*